United States Patent [19]

Bigou

[11] 4,002,758
[45] Jan. 11, 1977

[54] MEDICAMENT WHICH IS UTILIZABLE IN OPHTHALMOLOGY
[75] Inventor: Alphonse Bigou, Paris, France
[73] Assignee: Societe B.F.B., Champigny, France
[22] Filed: July 2, 1975
[21] Appl. No.: 592,513

Related U.S. Application Data
[63] Continuation of Ser. No. 403,172, Oct. 3, 1973, abandoned.

[52] U.S. Cl. .............................. 424/263; 424/319
[51] Int. Cl.² ....................................... A61K 31/44
[58] Field of Search .......................... 424/319, 263

[56] References Cited
OTHER PUBLICATIONS

Anderson et al., Chemical Abstracts 75:74064u (1971).
Maiorca et al., Chemical Abstracts 56:5350i–5351a (1962).
Denisova et al., Chemical Abstracts 71:59400z (1969).
Grosman et al., Chemical Abstracts 66:300t (1967).
Carminati – Chemical Abstracts 64 (14nnid) (1966).
Sturman et al., Chemical Abstracts 75:106850r (1971).
Engel et al., Chemical Abstracts 66:44618z (1967).
Poppe et al., Chemical Abstracts 76:13037m (1972).
Wilson et al., Textbook of Organic Medicinal and Pharm. Chem. 4th Edition (1962) p. 816.
Merck Index 8th Edition, (1968) p. 317.

*Primary Examiner*—Norman A. Drezin
*Attorney, Agent, or Firm*—Eyre, Mann, Lucas & Just

[57] ABSTRACT

A method of treating ophthalmological disorders is disclosed. The method comprises the oral administration from one to four times a day of a composition comprising:
  a. from 200 to 1,000 mg of a compound selected from the group consisting of cystine and cysteine
  b. from 50 to 300 mg of pyridoxine in the form of a base or a salt.

2 Claims, No Drawings

MEDICAMENT WHICH IS UTILIZABLE IN OPHTHALMOLOGY

This is a continuation of application Ser. No. 403,172, filed Oct. 3, 1973 and now abandoned.

The present invention relates to a novel medicament which is utilisable in ophthalmology and which comprises a combination of cystine and pyridoxine.

Cystine and/or cysteine or their derivatives are known sulphur-containing amino acids, which have found a certain number of uses as anticollagenasic agents.

It it also known that pyridoxine (vitamin $B_6$) in the form of the base or a salt has useful pharmacological properties. This vitamin has already been utilised in numerous medicaments.

It has now been found that the combination, in the same orally-administrable medicament, of cystine and/or cysteine with pyridoxine has unexpected beneficial results in ophthalmology and, in particular, upon disorders of the cornea in which there is lysis of collagen by the action of collagenase.

The invention thus relates to an orally-administrable medicament which comprises at the same time pyridoxine and from 1 to 10 parts by weight, with respect to the pyridoxine, of cystine and/or cysteine.

Utilisable doses of the medicament according to the invention depend upon the disorder to be treated, but it may be said that they are preferably such that the patient should be able to absorb 200 to 1,000 mg of cystine and/or cysteine and from 50 to 300 mg of pyridoxine per dose, such dose being repeated 2 to 4 times per day if necessary. A practical form of the composition of the invention thus comprises a dosage unit containing amounts of the components in the ranges stated.

The medicament according to the invention can be made up in the form of a coated tablet or pill or cachet or, in general, any form which can be taken orally. Clearly such pills can contain the ordinary excipients used, such as sugars, carboxymethylcellulose and talc for instance.

The pharmacological and toxicological properties of the two constituents of the medicament according to the invention are well known. It is known for instance that cystine and/or cysteine have no toxicity and that pyridoxine can be absorbed in relatively large quantities without showing marked undesirable secondary effects. The mixture according to the present medicament is virtually non-toxic.

The applications of the medicament according to the invention essentially relate to treatments of keratoconus, corneal injury or damage, corneal herpes, sub-epithelial viral keratitis and epidemic epithelial keratitis punctata. They also relate to the treatment of the difficulties caused by cicatrisation of the cornea and those due to non-tolerance by the cornea of contact lenses.

It may be noted that the action of the medicament according to the invention is clearly superior to the action of the constituents of such medicament when utilised alone. Cystine utilised alone has no action on the disorders mentioned previously and neither has pyridoxine and it can even be said that if there are administered to patients cachets of cystine on the one hand and cachets of pyridoxine on the other the action of the two medicaments is much less rapid than that of the medicament according to the invention.

It has been possible to show that, due to the simultaneous use of cystine and pyridoxine according to the invention, there is a remarkable synergistic action which leads to an excellent activity of the medicament in the region of the cornea.

Non-limitative examples illustrate the invention as follows:

1 — Study of the action of cystine-pyridoxine ($B_6$) compositions on injuries to rabbit corneas It is known that the application of 1% caustic soda solution to rabbit cornea causes serious lesions which become converted into partial or total opacities, more or less intense vascularisations and, frequently, perforation of the cornea.

Groups of rabbits which had undergone an application of caustic soda to the cornea were treated, immediately before such application, with:
 either 150 mg/kg by weight, 5 days per week and for 4 weeks, of cystine alone;
 or 180 mg/kg by weight, 5 days per week and for 4 weeks, of a mixture containing 150 mg of cystine and 30 mg of pyridoxine.

These groups each of eight rabbits were studied and compared with a control group comprising four rabbits which had received no treatment. In the control group, two of the four rabbits had had a perforation in the cornea after 19 days. The two other rabbits after 8 weeks (end of the experiment) had very extended and opaque leucomas covered with intense vascularisation. In the group of rabbits treated with cystine alone, it could be seen that there was no perforation of the cornea. Four rabbits had an opacity covering all the cornea, one rabbit had an intense vascularisation and five rabbits carried cicatricial labra or pads showing that the attack upon the collagen had had time to develop strongly before being stopped. With the group of rabbits treated with the cystine/pyridoxine composition, it could be seen that no rabbit had had any perforation of the cornea, only a single rabbit had an opacity covering all the cornea, no rabbit had any intense vascularisation and no rabbit was carrying any cicatricial labrum.

2 — Various applications

Coated tablets of cystine and pyridoxine corresponding to the following formula were made:

| | |
|---|---|
| cystine | 500 mg |
| pyridoxine (vitamin $B_6$) | 100 mg |
| lactose | |
| carboxymethylcellulose | sufficient quantities to |
| talc | give a tablet weighing |
| magnesium stearate | about 1 g |
| water | |

These tablets were coated with a known coating compound (Eudragit E, talc, gum arabic, sugar, tartrazine and yellow wax).

These tablets were administered to various patients at the rate of four tablets per day on average, as follows:
 Three cases of trophic troubles of the cornea had been able to recover owing to a sufficiently long treatment;
 Two cases of sub-epithelial viral keratitis had recovered owing to treatment which was carried out for 15 days;
 Sixteen cases of epidemic epithelial keratitis punctata had recovered by treatment for 1 week approximately, though with the medicaments at present known the healing could only be obtained after several weeks or even several months;

Fourteen cases of intolerance of corneal contact lenses had been treated. The patients had been able to continue to wear lenses throughout the treatment and the lenses had not needed to undergo any modification. At the end of the treatment, the patients could wear their lenses without inconvenience.

It is understood that the present invention includes any form of composition of cystine and pyridoxine in which those compounds are available.

I claim:

1. A method of treating ophthalmological disorders of the cornea in which there is lysis of collagen by the action of collagenase which comprises the oral administration to a patient in need thereof from one to four times a day of a composition comprising:
   a. from 200 to 1,000 mg of a compound selected from the group consisting of cystine and cysteine
   b. from 50 to 300 mg of pyridoxine in the form of a base or a salt.

2. A method of treating ophthalmological disorders of the cornea in which there is lysis of collagen by the action of collagenase which comprises the oral administration to a patient in need thereof from one to four times a day of a composition comprising:
   a. 500 mg of cystine
   b. 100 mg of pyridoxine.

* * * * *

UNITED STATES PATENT OFFICE
CERTIFICATE OF CORRECTION

PATENT NO. : 4,002,758
DATED : January 11, 1977
INVENTOR(S) : Alphonse Bigou

It is certified that error appears in the above-identified patent and that said Letters Patent are hereby corrected as shown below:

On the title page add the following:

--Foreign Application Priority Data:

October 13, 1972 .......France.........72/36441--

Signed and Sealed this

Eighth Day of February 1983

[SEAL]

Attest:

*Attesting Officer*

GERALD J. MOSSINGHOFF

*Commissioner of Patents and Trademarks*